(12) United States Patent
Lemaux et al.

(10) Patent No.: US 6,951,972 B1
(45) Date of Patent: Oct. 4, 2005

(54) TRANSPOSON TAGGING AND GENE DELIVERY IN SMALL GRAIN CEREALS

(75) Inventors: Peggy Lemaux, Moraga, CA (US); David McElroy, North Stonington, CT (US); Thomas Koprek, Pleasant Hill, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/384,811

(22) Filed: Aug. 27, 1999

Related U.S. Application Data

(60) Provisional application No. 60/098,221, filed on Aug. 28, 1998.

(51) Int. Cl.⁷ ............................................. C12N 15/82
(52) U.S. Cl. ..................................................... 800/291
(58) Field of Search ................................ 800/291, 320, 800/293, 298; 536/23.1, 23.2, 23.6; 435/320.1, 419, 468, 470

(56) References Cited

U.S. PATENT DOCUMENTS

| 4,732,856 A | 3/1988 | Federoff |
| 5,225,341 A | 7/1993 | Yoder et al. |
| 5,482,852 A | 1/1996 | Yoder et al. |

FOREIGN PATENT DOCUMENTS

WO    WO 92/01370    2/1992

OTHER PUBLICATIONS

Wan et al, "Generation of Large Numbers of Independently Transformed Fertile Barley Plants", 1994, Plant Physiol, vol. 104:37–48, pp. 37–48.*
Brancroft et al., "Development of an efficient two–element transposon tagging system in *Arabidopsis thaliana*", 1992, Mol Gen Genet, vol. 233: 449–461.*
Schulze et al., Stable transformation of barley using a highly–efficient protoplast system. Physiologia Plantarum, 1991, vol. 82, No. 1, pp. A32).*
Lazzeri et al., Stable transformation of barley via PEG–induced direct DNA uptake into protoplasts. Theor. Appl. Genet., 1991, vol. 81, pp. 437–444.*
Ritala et al., Stable transformation of barley tissue culture by particle bombardment. Plant Cell Reports, 1993, vol. 12, pp. 435–440.*
Stiff et al., Stable transformation of barley callus using biolistic particle bombardment and the phosphinothricin acetyltransferas (bar) gene. Plant Cell, Tissue and Organ Culture, 1995, vol. 40, pp. 243–248.*
Zhang et al., Parameters influencing transient and stable transformation of barely (Hordeum vulgare L.) protoplasts. Plant Cell, Tissue and Organ Culture, 1995, vol. 41, pp. 125–138.*

Ritala et al., Fertile transgenic barley by particle bombardment of immature embryos. Plant Molecular Biology, 1994, vol. 24, pp. 317–325.*
Funatsuki et al., Fertile transgenic barley generated by direct DNA transfer to protoplasts. Theor. Appl. Genet., 1995, vol. 91, pp. 707–712.*
Koprek et al., Fertile transgenic barley of different cultivars obtained by adjustment of bombardment conditions to tissue response. Plant Science, 1996, vol. 119, pp. 79–91.*
Brinch–Pedersen et al., Engineering of the aspartate family biosynthetic pathway in barley by transformation with heterologous genes encoding feed–back–insensitive aspartate kinase and dihydro . . . Plant Molecular Biology, 1996, vol. 32, pp. 611–620.*
Jensen et al., Transgenic barley expressing a protein–engineered, thermostable (1,3–1,4)–B–glucanase during germination. Pro Natl. Acad. Sci. USA, 1996, vol. 93, pp. 3487–3491.*
Koprek et al., Transposon–mediated single–copy gene delivery leads to increased transgene expression stability in barley. Plan Physiol. 125:1354–1362 (2001).*
McElroy et al. Development of a simple transient assay for Ac/Ds activity in cells of intact barley tissue. The Plant Journal, 1997 vol. 11, No. 1, pp. 157–165.*
Wan et al. Generation of Large Numbers of Independently Transformed Fertile Barley Plants. Plant Physiol., 1994, vol. 104, pp. 37–48.*
Bancroft et al. Development of an efficient two–element transposon tagging system in *Arabidopsis thaliana*. Mol. Gen. Genet., 1992, vol. 233, 449–461.*
Ritala et al. Fertile transgenic barley by particle bombardment of immature embryos. Plant Molecular Biology, 1994, vol. 24, pp. 317–325.*
Funatsuki et al., Fertile transgenic barley generated by direct DNA transfer to protoplasts. Theor. Appl. Genet., 1995, vol. 91, pp. 707–712.*
Koprek et al. Fertile transgenic barley of different cultivars obtained by adjustment of bombardement conditions to tissue response. Plant Science, 1996, vol. 119, pp. 79–91.*
Brinch–Pedersen et al. Engineering of the aspartate family biosynthetic pathway in barley by transformation with heterologous genes encoding feed–back–insensitive aspartate kinase and dihydro. . . Plant Molecular Biology, 1996, vol. 32, pp. 611–620.*

(Continued)

*Primary Examiner*—Amy J. Nelson
*Assistant Examiner*—Cynthia Collins
(74) *Attorney, Agent, or Firm*—Townsend & Townsend & Crew

(57) ABSTRACT

The disclosed discovery relates to the functioning of the Ac-Ds transposon system in small grain cereals such as barley, wheat, and oat. Methods and compositions for using this system for introducing recombinant expression cassettes and transposon tagging of genes in small grain cereals are provided.

7 Claims, 1 Drawing Sheet

OTHER PUBLICATIONS

Jensen et al., Transgenic barley expressing a protein–engineered, thermostable (1,3–1,4)–B–glucanase during germination. Pro Natl. Acad. Sci. USA, 1996, vol. 93, pp. 3487–3491.*

Perera et al. Cytosine deaminase as a negative selective marker for *Arabidopsis*. Plant Molecular Biology, 1993, vol. 23, p. 793–799.*

Aarts, M.G.M. et al., *Nature* (1993) 363: 715–717.

Baker et al., *Proc. Natl. Acad. Sci. USA* (1986) 83: 4844–4848.

Bancroft, I. et al., *Plant Cell* (1993) 5:631–638.

Chuck, G. et al., *Plant Cell* (1993) 5:371–378.

Ellis, J.G. et al., *Theor. Appl. Genet.* (1992) 85: 46–54.

Gerats, A.G.M. et al., *Dev. Genet.* (1989) 10: 561–568.

Haring, M.A. et al., *Plant Mol. Biol.* (1989) 13: 189–201.

Hehl, R. and Baker, B., *Plant Cell* (1990) 2: 709–822.

Izawa et al., *Plant Mol. Biol.* (1997) 35: 219–229.

Jones et al., *Science* (1989) 244: 204–207.

Jones et al., *Maydica* (1991) 36: 329–335.

Jones, J.D.G. et al., *4th Internatl. Congr. Plant Mol. Biol.*, Amsterdam, Jun. 19–24 (ISPMB), abs.: 1624 (1994).

Knapp, S. et al., *Mol. Gen. Genet.* (1988) 213:285–290.

Lawrence, G. et al., *Plant J.* (1993) 4 659–669.

Lawrence, J.G. et al., "Cloning a rust resistance gene in flax," *Seventh Int'l Symp. on Molecular Plant–Microbe Interactions*, Univ. Edin., Scotland, Jun. 26–Jul. 1, abs.: 287 (1994).

McElroy et al., *Plant Journal* (1997) 11: 157–165.

Rommens et al., *Mol. Gen. Genet.* (1992) 231L 433–441.

Scofield et al., *Plant Cell* (1992) 4: 573–582.

Van Sluys, M.A. et al., *EMBOJ* (1987) 6: 3881–3889.

Whitham, S. et al., *Cell* (1994) 78: 1101–1115.

Yang, C.H. et al., *Plant Mol. Biol.* (1993) 22: 793–805.

Yoder, J.L. et al., *Mol. Gen. Genet.* (1988) 213–291–296.

Zhou, J.H. et al., *Plant Cell Rep.* (1990) 8: 542–545.

J. Laufs et al., *Proceedings of the National Academy of Sciences of the USA* (1990) 87: 7752–7756.

R.J. Perera et al., *Plant Molecular Biology* (1993) 23: 793–799.

S. Takumi et al., *Theor. Appl. Genet.* (1999) 98:947–953.

Murai et al., "Transposition of the maize activator element in transgenic rice plants," *Nucleic Acids Research* (1991) 19(3): 617622.

Shimamoto et al., "Trans–activation and stable integration of the maize transposable element Ds cotransfected with the Ac transposase gene in transgenic rice plants," *Mol. Gen. Genet.* (1993) 239: 354–360.

* cited by examiner

TRANSPOSON TAGGING AND GENE DELIVERY IN SMALL GRAIN CEREALS

CROSS REFRENCE TO RELATED APPLICATIONS

This is application claims priority to U.S. Ser. No. 60/098,221, filed Aug. 28, 1998, which is incorporated by reference.

STATEMENT OF GOVERNMENT RIGHTS

The research underlying this invention was funded in part by the U.S. Department of Agriculture under grant number 440376-32261 JS43; the U.S. Government may have certain rights in this invention.

FIELD OF THE INVENTION

This invention relates to the use of the maize Ac/Ds transposon system in small grain cereals, including, for example, barley (*Hoirdium vulgare*), wheat, and oats.

BACKGROUND OF THE INVENTION

Insertional mutagenesis has been a valuable toot for creating and subsequently cloning genes for which no gene product is known. *Agrobacterium* T-DNA insertion has been successfully used as a mutagen in dicot plant species. However, T-DNA insertion is irreversible, excluding the use of T-DNA tagging systems to generate phenotypic revertants or new mutant alleles following excision and re-insertion. Furthermore, most cereals are not yet routinely transformable with *Agrobacterium*. DNA elements, able to insert at random in chromosomal DNA, e.g., transposons, are effective insertional mutagens.

Transposable elements (TEs), or transposons, first discovered in maize, are mobile genetic factors that move around the genome. The preference of certain TEs to move to linked sites (Dooner et al., 1989) makes it possible to map the initial introduced elements and use these mapped elements to generate secondary transpositions into nearby genes of interest. The insertion site and related gene can then be readily recovered using standard cloning or PCR-based procedures.

TEs can also be used for gene transfer to introduce a heterologous nucleic acid sequence into cereal plants. The advantages of such a gene delivery system are that: 1) the transgene of interest is physically moved away from the selection gene; 2) the generation of large numbers of plants with single copies of the transgene inserted in different chromosomal locations requires only two primary transformation events; and 3) the potential exists for the transgene to move to a genomic location that supports stable expression.

TEs occur in families of related sequences, defined by their ability to interact genetically. Within any one family, individual elements occur in two forms: one a structurally conserved element capable of promoting its own excision, termed the "autonomous" element, the other a structurally heterogeneous group of elements unable to promote their own excision, the so-called "non-autonomous" elements. Non-autonomous elements from one family can be trans-activated only by the autonomous member of the same family. Examples of such families of plant TEs include Activator-Dissociation (AciDs), EnhancerInhibitor/Suppressor-mutator (En/Spin) and Mutator (Mu/dMu) from maize and Transposon Antirrhinum majus (Tam) from Antirrhinurn majus. Analysis of isolated maize TE sequences revealed that they are flanked by short terminal inverted repeat sequences (cis-determinants) that are essential for transposition. Furthermore, the autonomous member of a TE family encodes a trans-acting factor (transposase) that is required for transposition.

TEs can either excise somatically, giving rise to sectors of various phenotypes in the plant body, or germinally, in either cell lineages that undergo meiosis or in the gametes themselves. Somatic excision of a TE from a gene whose phenotype can be readily visualized can result in a variegated pattern of excision-mediated gene expression, with clonal sectors of revertant cells on a mutant background. The size and shape of clonal sectors of revertant cells are determined by the developmental timing of TE excision and by the pattern of cell division within the host tissue (for a review, see Federoff, 1989). Progeny from a plant in which the TE has undergone germinal excision-mediated reversion will have a stable phenotype, ranging from null to full function depending on the "footprint" left behind by the transposon. These "footprints" result from excision-mediated deletions and/or non-template base additions. TEs themselves can undergo deletions, internal rearrangements and/or methylation-mediated inactivation converting an autonomous element into a non-autonomous element and/or altering the trans-activation pattern of non-autonomous elements.

Use of transposons to tag genes in plants was first applied to facilitate gene cloning in maize and Antirrhinurn where mutated alleles were already available and their endogenous TEs were well-characterized at both the genetic and molecular levels. For most higher plant species however, active transposons are either not available or not sufficiently characterized to be used to generate mutants or as gene delivery vehicles. Therefore, maize transposons have been used. Maize Ac was the first to be introduced successfully into a heterologous host, tobacco (Baker et al., 1986) Subsequently, the Ac-Ds system was used in other dicotyledenous species, including *Arabidopsis thalliana* and carrot (Van Sluys et al., 1987), potato (Knapp et al., 1988), tomato (Yoder et al., 1988), petunia (Gerats et al., 1989; Haring et al., 1989), soybean (Zhou et al., 1990), flax (Ellis et al., 1992; Lawrence et al., 1994), and lettuce (Yang et al., 1993).

The Ac-Ds transposable element system has been used in dicots to tag genes. Examples include the N viral resistance gene from tobacco (Whitham et al., 1994, U.S. Pat. No. 5,571,706), the petunia Ph6 coloration gene (Chuck et al., 1993), the tomato Cf-9 fungal resistance gene (Jones et al., 1994), the flax L6 gene for rust resistance (Lawrence et al., 1993) and developmental (Bancroft et al., 1993) and male-sterility (Aarts et al., 1993) genes from *Arabidopsis*.

In addition to gene tagging, the Ac-Ds system has been proposed as a means of obtaining transgenic plants that are free of potentially problematic selectable marker genes that are typically used in transformation vectors (see U.S. Pat. Nos. 5,225,341 and 5,482,852). This strategy incorporates the transgene of interest into a Ds element, and introduces the construct either into plants that already contain an Ac-transposase gene, or co-transforms this construct with an Ac-transposase gene into the plant species of interest. Alternatively, a plant containing the Ds element including the transgene may be crossed with a plant containing the Ac-transposase gene. Subsequent transposition of the Ds element carrying the gene of interest to a site that is unlinked to the transformation vector sequences permits progeny plants carrying only the Ds element to be selected. Such progeny plants do not carry the transformation vector backbone or associated selectable markers.

Despite the reported successes of the Ac-Ds system in dicotyledenous plant species, the successful stable introduction of these elements into monocotyledenous species has been limited to rice (for a review, see Izawa et al., 1997). In that species, problems associated with too frequent excision of Ds elements in the F, generation, coupled with inactivation of the elements in later generations, have hampered efforts to use the system to tag genes (Izawa et al., 1997). Recently, a transient assay system for monitoring the activity of the Ac-Ds system in barley was reported (McElroy et al., 1997). While that report indicated that the Ac transposase was active and could cause excision of a Ds element in barley cells, the transient nature of the assay system did not address whether this transposon system could be effectively used in stable barley transformants for gene tagging or delivery. For example, it did not address whether the problems reported in stable transformants in rice might also be problematic in barley. Critically, it also did not indicate that excised Ds elements could re-integrate into the barley genome, a feature vital for effective transposon tagging or gene delivery.

SUMMARY OF THE INVENTION

The present inventors have shown for the first time that the maize Ac/Ds transposable element system is active in stably transformed barley, and have demonstrated that Ds elements can excise from one position in the genome and integrate at another. In some instances, reintegration of the Ds element occurs at sites in the genome that are unlinked to the original (excision) site; in other cases the sites are linked. Thus, the inventors have discovered that the Ac/Ds system may be used to tag genes in barley and other cereals such as wheat and oats, and may be used for delivering transgenes to new genomic locations.

The latter capability can be used to obtain integration of a transgene-contained within a Ds element (a "Ds-transgene") at a position unlinked to the site at which the transformation vector originally integrated. This means that in subsequent generations, plants may be obtained that contain only the Ds-transgene and not the other nucleic acid sequences contained in the original transformation vector. This approach will be particularly useful for obtaining transgenic plants that express a beneficial transgene but do not contain the selectable resistance or screenable markers used in the transformation vector.

The invention thus provides small grain cereal plants, such as barley, wheat, and oat, containing an Ac and/or Ds element, as well as methods of producing transgenic plants that have integrated Ds elements capable of excising and reinserting into the genome at a new location. Such plants include, for example, barley plants having stable insertion mutations. Thus, among other aspects, the invention provides a small grain cereal plant, preferably barley, wheat, or oat, comprising at least one Ds element integrated into its genome, wherein the Ds element is integrated into the genome at a position to which the element transposed (rather than the site at which the transformation vector integrated). In particular embodiments, the Ds element is integrated at a genomic position that is unlinked to the position from which the element transposed. In some instances, the Ds element may include a heterologous gene sequence, such as the bar herbicide resistance gene or other gene of interest.

The invention also provides a method of mobilizing a Ds element that is integrated in the genome of a barley, or other small grain cereal plant, by supplying an Ac transposase enzyme to the Ds element. The Ac transposase may be encoded by a construct that comprises the open reading frame of the transposase operably linked to a promoter sequence that is active in the cereal, or the intact Ac element may be used.

With respect to transposon tagging, the invention provides a method of creating an insertional mutation in a small grain cereal plant, the method comprising introducing into a cereal plant, for example barley or wheat, at least one copy of a nucleic acid encoding maize Ac transposase and at least one Ds element or another gene, enclosed in the Ds ends. While this two element system is likely to be advantageous because of the ability to stabilize a Ds insertion by outcrossing to remove the transposase gene, transposon tagging in small grain cereals may also be effected using a single Ac element approach. In such instances, the single Ac element or a vector containing transposase and a functional Ds element in the same plasmid, minimally encodes a functional transposase and includes the terminal repeat sequences necessary for transposition. In this respect, the invention also provides a method of creating an insertional mutation in a cereal plant, e.g., barley, the method comprising introducing into a cereal plant at least one Ac element.

Other aspects of the invention include alternative methods of obtaining an insertion mutation in a cereal plant, preferably barley, wheat or oat, using the Ac-Ds system. One such embodiment involves crossing a first generation cereal plant carrying at least one nucleic acid-molecule encoding an Ac transposase with a first generation cereal plant carrying at least one Ds element; and then selecting at least one second generation progeny plant carrying at least one nucleic acid molecule encoding an Ac transposase and at least one Ds element. This method may further comprise breeding the selected first generation progeny plant by selfing or out-crossing; and then obtaining at least one second generation progeny plant that carries at least one Ds element, wherein the Ds element has transposed within the genome of the cereal plant. In particular embodiments, the selected second generation progeny plant contains no Ac transposase sequences. Crossing procedures such as these may also be carried out using later generation plants.

The invention also encompasses a method for identifying and isolating a gene in a cereal plant such as barley, wheat or oat, the method comprising providing a cereal plant having an insertional mutation resulting from the insertion of an Ac or a Ds element, and isolating the cereal gene into which the Ac or Ds element is inserted. Also encompassed by the invention is a cereal gene isolated according to this method.

These and other aspects of the invention are described in more detail below.

DETAILED DESCRIPTION OF THE INVENTION

I. Definitions

Figure 1:
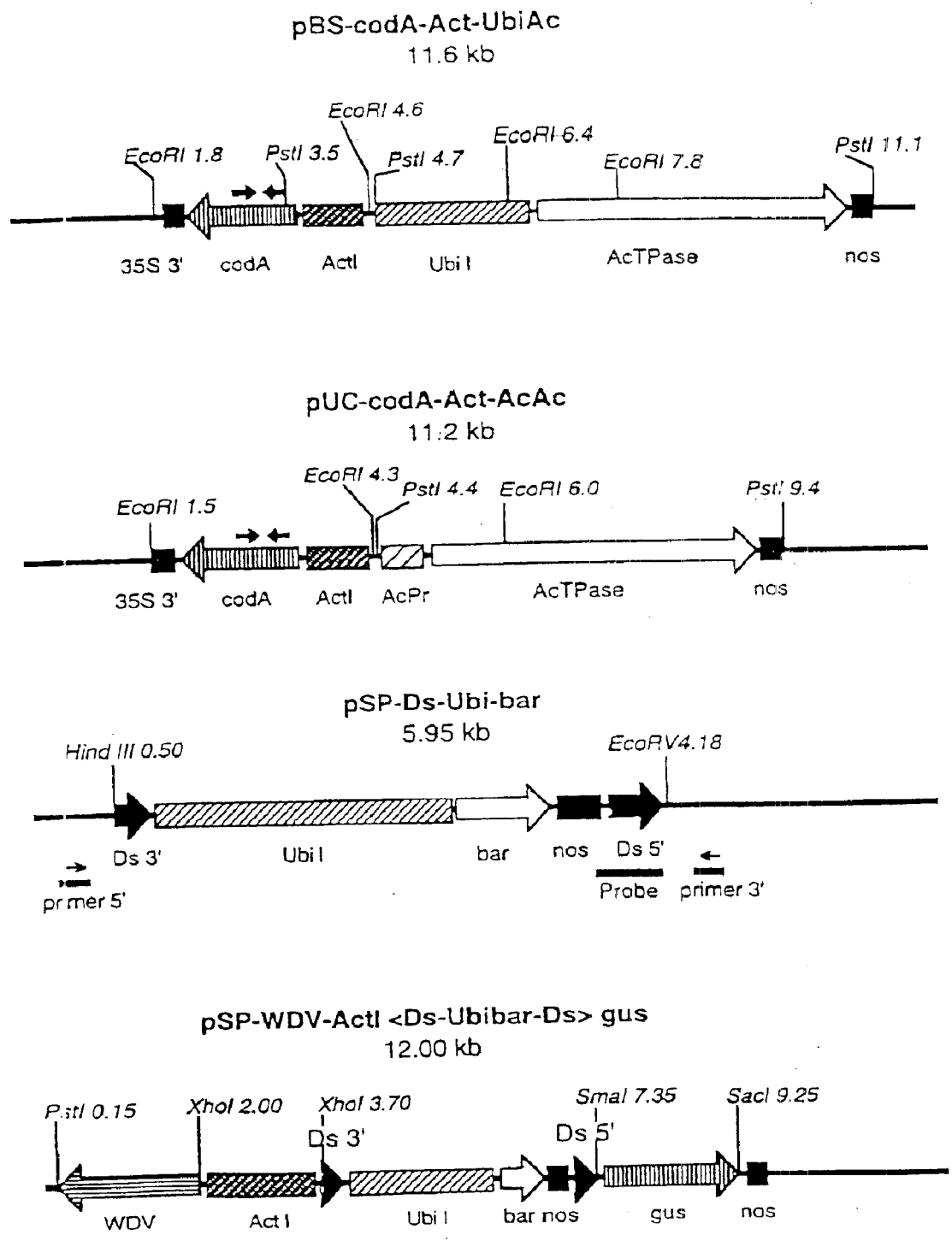
FIG. 1 shows schematic representations of vectors used in certain embodiments of the invention.

Unless otherwise noted, technical terms are used according to conventional usage. Definitions of common terms in molecular biology maybe found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of the invention, the following definitions of terms are provided:

Ac: the maize Ac element has been extensively characterized (see, for example Federoff, 1989, Gierl and Sadler, 1992, Coupland et al., 1988). The 4.6 kb autonomous Ac element encodes an active transposase (contained on a 3.5 kb transcript), whereas the non-autonomous Ds elements carry internal deletions and can only transpose when the Ac transposase is provided in trans. Transposition of the Ac element requires the presence of the 11 bp inverted terminal repeats that are present at each end of the element. The Ac transposase may be provided in trans in a plant by introducing a fully functional Ac element, by introducing a crippled Ac element (lacking one or both of the terminal repeat regions), or by introducing the transposase open reading frame operably linked to a promoter sequence. Suitable promoters include the cauliflower mosaic virus 35S promoter, and the native Ac transposase promoter (see, for example, Shimamoto et al., 1993; McElroy et al., 1997). As used herein, the term "Ac element" refers to an intact autonomous Ac transposon, whereas the term "a nucleic acid molecule encoding an Ac transposase" refers to any nucleic acid molecule that encodes a functional transposase enzyme. A functional transposase enzyme is one that can transactivate a Ds element in barley or other cereals; this may be conveniently determined using the transient assay described by McElroy et al., 1997.

Ds element: Ds elements do not encode a functional Ac transposase, but they do include the inverted terminal repeat sequences and associated sequences that are required for transactivation by an Ac transposase (see Federoff, 1989, Gierl and Sadler, 1992, Coupland et al., 1988). Ds elements may be engineered to carry heterologous nucleic acid sequences between their terminal repeats, as described in U.S. Pat. Nos. 5,225,341 and 5,482,852. As used herein, the term "Ds element" refers to any form of Ds non-autonomous element that can transpose in small grain cereals such as barley, wheat, or oat, including forms of Ds carrying heterologous sequences between the terminal repeats. The ability of a Ds element to transpose under the influence of a trans-acting Ac transposase may be conveniently determined using the transient assay described by McElroy et al., 1997.

Heterologous: A polynucleotide sequence is "heterologous to" an organism or a second polynucleotide sequence if it originates from a foreign species, or, if from the same species, is modified from its original form (e.g. does not naturally occur linked to the second sequence). For example, a transposon comprising a heterologous sequence refers to a transposon comprising a sequence that is not naturally linked to the transposon, but is inserted into the transposon as a result of genetic engineering techniques. The inserted sequence is typically a recombinant expression cassette.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., 1989 and Ausubel et al., 1987. Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al., 1989, Ausubel et al., 1987, and Innis et al., 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the maize Ac sequence will anneal to a related target sequence with a higher specificity than a corresponding primer of only 15 nucleotides. Thus, in order to obtain greater specificity, probes and primers may be selected that comprise 20, 25, 30, 35, 40, 50 or more consecutive nucleotides of a selected sequence.

Oligonucleotide: A linear polynucleotide sequence of up to about 100 nucleotide bases in length.

Vector: A nucleic acid molecule as introduced into a host cell, thereby-producing a transformed host cell. A vector may include nucleic acid sequences that permit it to replicate in a host cell, such as an origin of replication. A vector may also include one or more selectable marker genes and other-genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, *Agrobacterium* infection, and particle gun acceleration. Methods for transformation of barley include those described by Wan et al., 1994, Lemaux et al., 1996, and Tingay et al., 1997.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified protein preparation is one in which the subject protein is more enriched than the protein is in its natural environment within a cell. Generally, a preparation of a protein is purified such that the subject protein represents at least 50% of the total protein content of the preparation. For particular applications, higher purity may be desired, such that preparations in which the subject protein represents at least 75% or at least 90% of the total protein content may be employed.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or desirable, join two protein-coding regions, in the same-reading frame.

Recombinant: A recombinant nucleic acid is one that has a sequence that is not naturally occurring or has a sequence that is made by an artificial combination of two otherwise separated segments of sequence. This artificial-combination is often accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

II. Use of the Ac-Ds System in Small Grain Cereals

The inventors have shown three prerequisites for the use of Ac-Ds elements in cereals such as barley, wheat or oat that were previously unknown: (1) that Ac-transposase can trans-activate Ds elements in stably transformed barley, (2) that trans-activated Ds elements re-integrate into the barley genome, and (3) that Ac-transposase can trans-activate Ds in immature embryos of wheat in transient assays. Based on these discoveries, the use of the Ac-Ds system in stably transformed cereals such as barley, wheat, and oat, can now be effected. Exemplary applications of this system in these cereals are gene tagging and the introduction of heterologous nucleic acid sequences into the plant in single copies.

For example, the Ac-Ds system may be employed in barley, wheat, or oat to introduce heterologous gene sequences that do not include selectable marker genes used in transformation vectors, using the approached described by Yoder et al. in U.S. Pat. Nos. 5,225,341 and 5,482,852.

Means for introducing heterologous recombinant expression cassettes into small grain cereals are known. These methods include bombardment-mediated techniques (see, e.g. Lemaux et al., 1996), electroporation (see, e.g., Salmenkallio-Marttila et al., 1995), or *Agrobacterium* infection (see, e.g., Tingay et al., 1997).

In these embodiments, a DNA construct comprising a transposon containing an expression cassette designed for initiating transcription or translation of a polynucleotide of interest is introduced into cereal plants. Such polynucleotides can, for example include P-amylase (see, e.g., Kihara et al., 1997), lipoxygenase (see, e.g., Voeroes et al., 1998), and β-glucanase (see, e.g., Jensen et al., 1998) for barley; and wheat-starch-branching enzyme (see, e.g., Rahman et al., 1999), ADP-glucose pyrophosphorylase (see, e.g., Lalonde et al., 1997), and waxy (see, e.g., Miura et al., 1994) for wheat. The construct will also typically contain an ancillary selectable marker gene by which transformed plant cells can be identified in culture. Usually, the marker gene will encode antibiotic or herbicide resistance. These markers include resistance to G418, hygromycin, bleomycin, kanamycin, methotrexate, chlorsulfuron, lincomycin, clindamycin, spectinomycin, phosphinotricin, glyphosate and gentamicin. After transforming the plant cells, those cells that have the vector and express the selectable transgene will be identified by their ability to grow on a medium containing the particular antibiotic or herbicide.

For expression in plants, the recombinant expression cassette will typically contain in addition to the desired sequence, a plant promoter region, an intron (particularly in monocots), a transcription initiation site (if the sequence to be transcribed lacks one), and a transcription termination sequence. Unique restriction enzyme sites at the 5' and 3' ends of the cassette are typically included to allow for easy insertion into a pre-existing vector.

The particular promoter used in the expression cassette is not a critical aspect of the invention. Any of a number of promoters which direct transcription in plant cells is suitable. For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Alternatively, the plant promoter may direct expression of the heterologous nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well. In monocots, intron regions are often included between the promoter and the transgene in order to enhance expression. Examples of such introns are the maize ubiquitin 1 intron and the rice actin intron.

If proper polypeptide expression is desired, a polyadenylation region at the 3'-end of the coding region should be included. The polyadenylation region can be derived from the natural gene, from a variety of other plant genes, or from T-DNA.

The expression cassettes of the invention need not encode functional polypeptides and can be used, for example, to control, transcription, RNA accumulation, translation, and the like of endogenous genes.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque, 1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al., 1997) and by preventing the accumulation of mRNA which encodes the protein of interest, (see, Baulcombe, 1996; Prins and Goldbach, 1996; Metzlaff et al., 1997, Sheehy et al., 1988, and Hiatt et al., U.S. Pat. No. 4,801,340).

Oligonucleotide-based triple-helix formation can also be used to disrupt gene expression. Triplex DNA can inhibit DNA transcription and replication, generate site-specific mutations, cleave DNA, and induce homologous recombination (see, e.g., Havre and Glazer, 1993; Scanlon et al., 1995; Giovannangeli et al., 1996; Chan and Glazer, 1997). Triple helix DNAs can be used to target the same sequences identified for In antisense regulation.

Catalytic RNA molecules or ribozymes can also be used to inhibit expression of endogenous genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation. The design and use of target RNA-specific ribozymes is described in Zhao and Pick, 1993; Eastham and Ahlering, 1996; Sokol and Murray, 1996; Sun et al., 1997; and Haseloff et al., 1988).

Another method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al., 1993; Flavell, 1994; Stam et al., 1997; Napoli et al., 1990; and U.S. Pat. Nos. 5,034,323, 5,231,020, and 5,283,184).

After transformation, transformed plant cells or plants containing the desired gene must be identified. A selectable marker, such as those discussed, supra, is typically used. Transformed plant cells can be selected by growing the cells on growth medium containing the appropriate antibiotic. Means for regenerating transgenic cereal plants, e.g., barley, are described, for example, in Jahne et al., 1994).

Once a plant has been transformed so that the recombinant expression cassette of interest, the transposon and ancillary foreign nucleic acids are incorporated into the genome of the plant, the transformed plant is crossed to another plant expressing recombinant transposase in order to eliminate the ancillary sequences from the plant as described by Yoder in U.S. Pat. Nos. 5,225,341 and 5,482,852.

III. Gene Tagging

Gene tagging in small grain cereals can now be accomplished using methods similar to those that have been previously described for dicot plants (Whitham et al., 1994; U.S. Pat. No. 5,571,706; Chuck et al., 1993; Jones et al., 1994; Lawrence et al., 1993; Bancroft et al., 1993; Aarts et al., 1993) and rice (Izawa et al., 1997), and those described by Federoff in U.S. Pat. No. 4,732,856. While the examples described above utilized the dual element Ac-Ds system, tagging could also be performed using a single Ac element system. However, such a system may be less desirable than the two element approach because insertion mutants would be unstable given that the Ac element is capable of autonomous transposition, making tagged genes more difficult to identify and isolate.

The two element Ac-Ds system in which the trans-activating transposase is provided not by an autonomous Ac element, but rather by a nucleic acid molecule encoding the Ac-transposase in a separate vector, is likely to be a more useful system for gene isolation. Various forms of Ac-transposase nucleic acids may be employed, including Ac elements lacking terminal repeats, and the Ac-transposase open reading frame operably linked to a promoter sequence. Similarly, a number of Ds elements have been described (see, for example, Lassner et al., 1989; Yoder et al., 1989). Schemes for transposon tagging are well known. As applied to cereals, a typical scheme involves introducing Ac-transposase and Ds constructs separately into cereals using known transformation techniques, to produce $T_0$ ines. These plants may be selfed to produce $T_1$ plants that are analyzed by Southern blotting or PCR to verify the presence of the introduced construct. Lines carrying the Ac-transposase and the Ds constructs are then crossed to produce $F_1$ progeny. The $F_1$ progeny may be analyzed for molecular evidence of transposition of the Ds elements (by Southern blotting or PCR), and these lines may either be screened for mutations, or may be selfed to produce an $F_2$ generation that is screened for mutations, the tagged gene being more easily identified in the $F_2$ populations. Typically, the $F_2$ generation will include plants that are homozygous for Ds insertions, allowing recessive mutations to be detected. The type of mutation screen employed will vary depending on the type of mutation that is being sought. For example, if one is looking for a cereal plant such as a barley plant that produces seeds earlier in the growing season, then visual inspection of the crop during the growing season could be used as a simple screen. On the other hand, the seeds might be sown in medium having an acidic pH to select for plants that have enhanced ability to grow in acidic soils. In addition, the $F_2$ population plants will be identified in which only the Ds element with its associated sequences is present.

Once a plant having a particular desired phenotype has been selected, it is selfed and the progeny analyzed for co-segregation of a particular Ds insertion with the desired phenotype. Thereafter techniques such as IPCR (Earp et al., 1990) may be employed in conjunction with primers that read out from the Ds element to clone plant, e.g., barley, sequences that flank the Ds element. These barley sequences may then be used to confirm segregation of the inserted Ds element with the observed phenotype. The barley gene containing the cloned flanking regions may then be cloned using conventional techniques such as PCR or hybridization with a barley genomic library.

In particular embodiments, it may be advantageous to select plants that contain the desired Ds insertion but lack the Ac-transposase sequence, to avoid complications caused by continued transposition of the Ds element (see U.S. Pat. Nos. 5,225,341 and 5,482,852). This may be achieved by outcrossing the plant containing the Ds-tagged gene and screening progeny plants by Southern hybridization or PCR to obtain progeny plants that carry the Ds-tagged gene but not the Ac-transposase sequences. This screening may be facilitated by use of an Ac-transposase construct that is linked to a negative selectable marker, such as coda (Stougaard, 1993), as illustrated in FIG. 1b and FIG. 1c. In such instances, plants carrying the Ac-transposase may be killed by application of the appropriate agent for the negative selectable marker gene (in the case of CodA, 5-fluorocytosine), leaving a population of plants that is then screened for the presence of the Ds-tagged gene.

IV. Introducing Tagged Genes into Plants

Once a cereal, e.g. barley, wheat, or oat, gene encoding a protein involved in the determination of a particular plant characteristic has been tagged using the described Ac-Ds system, the gene or its corresponding cDNA may be isolated and introduced into a barley, wheat, or oat plant, or other plant species, in order to modify that particular plant characteristic. The basic approach is to clone the cDNA or gene into a transformation vector, such that it is operably linked to control sequences (e.g., a promoter) that direct expression of the cDNA or gene in appropriate plant cells. The transformation vector is then introduced into plant cells by one of a number of techniques (e.g., electroporation, microparticle bombardment, or *Agrobacterium* infection) and progeny plants containing the introduced cDNA or gene are selected. Preferably, that part of the transformation vector containing the transgene of interest will stably integrate into the genome of the plant cell. That part of the transformation vector which integrates into the plant cell and which contains the introduced cDNA or gene and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA or gene cloned into the transformation vector or may be manifested as enhanced resistance to a chemical agent (such as an antibiotic or herbicide) as a result of the inclusion of a dominant selectable marker gene incorporated into the transformation vector.

Successful examples of the modification of plant characteristics by transformation with cloned cDNA or gene sequences are replete in the technical and scientific literature. Selected examples, which serve to illustrate the knowledge in this field of technology include:

U.S. Pat. No. 5,571,706 ("Pant Virus Resistance Gene and Methods")

U.S. Pat. No. 5,677,175 ("Plant Pathogen Induced Proteins")

U.S. Pat. No. 5,510,471 ("Chimeric Gene for the Transformation of Plants")

U.S. Pat. No. 5,750,386 ("Pathogen-Resistant Transgenic Plants")

U.S. Pat. No. 5,597,945 ("Plants Genetically Enhanced for Disease Resistance")

U.S. Pat. No. 5,589,615 ("Process for the Production of Transgenic Plants with Increased Nutritional Value Via the Expression of Modified 2S Storage Albumins")

U.S. Pat. No. 5,750,871 ("Transformation and Foreign Gene Expression in—Brassica Species")

U.S. Pat. No. 5,268,526 ("Overexpression of Phytochrome in Transgenic Plants")

U.S. Pat. No. 5,262,316 ("Genetically Transformed Pepper Plants and Methods for their Production")

U.S. Pat. No. 5,569,831 ("Transgenic Tomato Plants with Altered Polygalacturonase Isoforms").

These examples include descriptions of transformation vector selection, transformation techniques and the construction of constructs designed to over-express the introduced cDNA or gene. Genes and cDNAs isolated from small grain cereals using the described transposon tagging system may be introduced into plants to modify particular characteristics that are controlled by these sequences.

a. Plant Types

While the genes isolated from, e.g., barley by the described methods may be re-introduced in various forms into barley, the genes may also be usefully introduced into a wide range of other plant species including monocotyledonous and dicotyledenous plants, such as maize, wheat, oat, millet, rice, soybean, cotton, beans in general, rape/canola, alfalfa, flax, sunflower, safflower, brassica, tobacco, peanut, clover, cowpea, grapes; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; and flowers such as carnations and roses.

b. Vector Construction, Choice of Promoters

A number of recombinant vectors suitable for stable transfection of plant cells or for the establishment of transgenic plants have been described including those described in Weissbach and Weissbach, 1989, and Gelvin et al., 1990. Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally-or developmentally-regulated, or cell- or tissue-specific expression), an intron, a transcription initiation start site, a ribosome binding site, an RNA processing signal, a transcription termination site, and/or a polyadenylation signal.

Examples of constitutive plant promoters that may be useful for expressing the cDNA include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua, 1990); the nopaline synthase promoter (An et al., 1988); the octopine synthase promoter (Fromm et al, 1989), the maize ubiquitin 1 promoter and intron (Christensen and Quail, 1996) or the rice actin 1 promoter and intron (McElroy et al., 1991).

A variety of plant gene promoters that are regulated in response to environmental, hormonal, chemical, and/or developmental signals, also can be used for expression of the cDNA in plant cells, including promoters regulated by: (a) heat (Callis et al., 1988; Ainley, et al, 1993; Gilmartin et al., 1992); (b) light (e.g., the pea rbcS-3A promoter, Kuhlemeier et al, 1989, and the maize rbcS promoter, Schaffner and Sheen, 1991); (c) hormones, such as abscisic acid (Marcotte et al, 1989); (d) wounding (e.g., wunl, Siebertz et al., 1989); and (e) chemicals such as methyl jasminate or salicylic acid (see also Gatz et al., 1997).

Alternatively, tissue specific (root, leaf, flower, and seed for example) promoters (Carpenter et al., 1992, Denis et al., 1993, Opperman et al, 1993, Stockhause et al., 1997; Roshal et al, 1987; Schernthaner et al, 1988; Bustos et al., 1989; and Cho et al., 1999) can be fused to the coding sequence to obtained particular expression in respective organs.

Plant transformation vectors may also include RNA processing signals, for example, introns (such as the maize ubiquitin-1 intron and the rice actin-1 intron), which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

Finally, as noted above, plant transformation vectors may also include dominant selectable marker genes to allow for the ready selection of transformants. Such genes include those encoding antibiotic resistance genes (e.g. resistance to hygromycin, kanamycin, bleomycin, G418, streptomycin or spectinomycin) and herbicide resistance genes (e.g., phosphinothricin acetyltransferase).

c. Arrangement of Tagged Gene Sequence in Vector

The particular arrangement of the tagged gene sequence (or the corresponding cDNA) in the transformation vector will be selected according to the type of expression of the sequence that is desired.

Where enhanced expression of the tagged sequence is desired throughout the entire plant, the ORF of the tagged sequence may be operably linked to a constitutive high-level promoter such as the CaMV 35S, maize ubiquitin, or rice actin promoter. In contrast, reducing the expression of the native homolog of the tagged gene in the transgenic plant may be obtained by introducing into plants antisense constructs based on the tagged gene sequence. Use of antisense, ribozymes, and sense suppression constructs are described above.

Constructs expressing an untranslatable form of the tagged gene's mRNA may also be used to suppress the expression of the native homolog. Methods for producing such constructs are described in U.S. Pat. No. 5,583,021 to Dougherty et al. Preferably, such constructs are made by introducing a premature stop codon into the ORF of the tagged gene.

d. Transformation and Regeneration Techniques

Transformation and regeneration of both monocotyledonous and dicotyledonous plant cells is now routine, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium lumefaciens* (AT) mediated transformation. Typical procedures for transforming and regenerating plants are described in the patent documents listed at the beginning of this section.

e. Selection of Transformed Plants

Following transformation and regeneration of plants with the transformation vector, transformed plants are usually selected using a dominant selectable marker incorporated into the transformation vector. Typically, such a marker will confer antibiotic or herbicide resistance on the seedlings of transformed plants, and selection—of transformants can be accomplished, by exposing the seedlings to appropriate concentrations of the antibiotic or herbicide. Preferably, the selectable marker will be operably linked to the transgene of interest.

After transformed plants are selected and grown to maturity, they can be analyzed for phenotypic effects of the transformation process and the introduced sequences.

V. Examples

The data disclosed herein in Examples 1–6 demonstrate that the Ac transposase gene is stably expressed over several generations and that the expression level is sufficient to transactivate Ds elements in transient assays as well as in vivo.

Example 1

Generation of Barley Plants with a Stably Integrated Ac/Ds Maize TE System

Construction of Vectors

All DNA modifications were carried out according to standard protocols (Sambrook, 1989). The plasmids pUC-codA-Act-AcAc and pBS-codA-Act-UbiAc were generated by cloning a 3.6 kbp SmaI-BglII fragment, which was derived from pTps (Wirtz et al., 1997) and contained the Ac transposase coding region and nos terminator sequence, into either a pUC28- or pBS-derived plasmid. Each of these plasmids contains the codA coding region, which was cloned as a 1.3 kbp HindIII/-EcoRI fragment from pNE3 (kind gift of Dr. J. Stougaard), under the transcriptional control of the actin promoter ActI and first intron from rice (McElroy et al., 1990); and the nos terminator, which was derived from plasmid pNG72 (McElroy et al., 1995). Transcription of the Ac transposase coding region in the pUC28-derived plasmid is controlled by the Ac promoter contained in a 323 bp SacI-Bg/II fragment derived from plasmid pSLJ721 (Scofield et al., 1992), and, in the pBS-derived plasmid, is controlled by the Ubi1 promoter and first intron from maize (Christensen and Quail, 1996). Plasmid pSP-Ds-Ubi-bar contains the *S. hygroscopicus* phosphinothricin acetyl transferase gene (bar) and the nos terminator as a 0.9 kbp ClaI-NotI restriction fragment derived from pBARGUS (Fromm et at., 1990). The bar gene is under control of the Ubi1 promoter and first intron from maize, which was derived as a 2.0 kbp PstI fragment from plasmid pAHC27 (Christensen and Quail, 1996). The Ubi1-bar-nos cassette is flanked by 254 bp Ds 5' sequence and 320 bp Ds 3' sequence derived from pDs7 (Wirtz et al., 1997) as a 0.59 kbp SaII-BamHI restriction fragment. Plasmid pAHC20 (Christensen and Quail, 1996), containing the *S. hygroscopicus* phosphinothricin acetyl transferase gene (bar) under control of the Ubi 1 promoter and first intron from maize was used for selection after co-transformation with plasmids pUC-codA-Act-AcAc or pBS-codA-Act-UbiAc. FIG. 1 shows diagrams of all of the plasmids used in this study.

Plant Transformation and Regeneration

Barley (*Hordeum vulgare* L. cv Golden Promise) scutellar tissue was cultivated, transformed via particle bombardment and selected as described (Wan, 1994; Lemaux, 1996; Cho et al., 1998). Scutella were either transformed with, or co-transformed with, pAHC20 and pUC-codA-Act-AcAc, pAHC20 and/or pSP-Ds-Ubi-bar and pBS-codA-Act-UbiAc. $T_0$ plants were regenerated from stably transformed callus following the protocol of Cho et al., 1998. Phenotypically normal $T_0$ plants were transferred to soil and grown under greenhouse conditions (14 h light/10 h dark 15–18° C., natural and supplemental light levels at 700–1000 $\mu$mol/m$^2$/s).

DNA Blot Hybridization Analyses of Transformants

Genomic DNA was isolated from two leaves when the plants were in the three-leaf stage (Cone, K., 1989) and digested with either PstI to analyze whether the Ubi-Ac or Ac—Ac cassettes (6.0 kbp and 4.4 kbp, respectively) were intact, or with EcoRV and HindIII to release the intact Ds-Ubi-bar (3.6 kbp) cassette from Ds-positive plants. To detect transposition events and to determine the number of Ds copies, the DNA was digested with HindIII, which does not cut within the Ds-Ubi-bar cassette. Excision and reinsertion of a Ds element in a new location creates a new HindIII fragment that can be detected after hybridization with a Ds-Ubi-bar internal probe. Digested DNA was electrophoretically separated on 0.8% agarose gels and transferred to Zeta-Probe membranes (Bio Rad) according to the manufacturers recommendations. Membranes were hybridized with $^{32}$P-labeled probes and washed following the protocol of the manufacturer. The positions of the probes on the plasmid are indicated in FIG. 1. The probe for Ds-Ubi-bar was PCR-amplified using plasmid DNA pSP-Ds-Ubi-bar as a template for the primers described below and purified using the QIAquick PCR purification kit from Qiagen. Probe DsB was derived from restriction endonuclease-digested and electrophoretically-separated plasmid DNA. The probe was isolated from gel slices with the QIAquick gel extraction kit from Qiagen. Labeling of the probes was performed using the Promega Prime-a-Gene labeling kit (Promega, Madison, Wis.).

PCR Analysis of Transformants

DNA was isolated (Cone, K., 1989) from leaf tissue when plants were in the three-leaf stage and 0.1 $\mu$g of genomic DNA was subjected to PCR amplification in a MJ Research thermocycler (PTC-100). Fifty $\mu$l PCR reactions contained 1×PCR Buffer (Promega, Madison, Wis.), 200 $\mu$M of each dNTP, 1.5 mM $MgCl_2$, 1 $\mu$M primer, 1% DMSO and 2.5 U Taq DNA Polymerase (Promega, Madison, Wis.). The primer pairs used for the PCR analysis were: 1.) for the Ac transposase coding region, Ac5' (5'-AAC CTA TTT GAT GTT GAG GGA TGC-3') and Ac3' (5'-ACC AcC AGC AcT GAA CGC AGA CTC-3'), to produce an expected PCR product of 852 bp; and 2.) for DsA, bar5' (5'-TGC AcC ATC GTC AAC CAC TA-3') and Ds3' (5'-AAC GTC AGT AGG GC TAA TCT TTT-3') to produce a 650 bp PCR fragment. For analysis of empty donor sites, primers EDS5' (5'-CGT CAG GGC GCG TCA GCG GGT GTT-3') and EDS3' (5'-AAT AcG CAA AcC GCC TCT CCC CGC-3') were used to amplify a 300 bp fragment. PCR reactions were performed with an initial denaturation at 94° C. for 2 min followed by 10 cycles of a touch down program with decreasing annealing temperatures from 65 to 60° C. in increments of –0.5° C. per cycle for 45 sec, an extension at 72° C. for 60 sec, a denaturation at 94° C. for 45 sec, and subsequent 25 amplification cycles for 45 sec at 60° C., 60 sec at 72° C. and 45 sec at 94° C. and a final extension at 72° C. for 5 mm. PCR products were analyzed by gel electrophoresis in 1.1% agarose gels.

Maize Ac transposase or a Ds element containing bar were stably introduced into barley. A total of 44 independent transgenic barley lines, carrying either Ac transposase or Ds-ubi-bar or both elements, were generated. Only phenotypically normal plants with a low copy number of the intact introduced gene were used for further experiments.

Example 2

Expression of Ac Transposase in Stably Transformed Barley Plants

The expression of the stabilized Ac and the functionality of Ac transposase were monitored using a transient assay for Ac transposase activity in barley (McElroy, et al., 1997). T1/T2 immature embryos (1.5 to 3.0 mm in length) of plants confirmed molecularly as containing either AcAc-transposase or UbiAc-transposase were bombarded with a test construct carrying an ActI-gusA expression cassette interrupted by a Ds insert (FIG. 1, plasmid pSPWDV-Act1 (Dsbar)-GUS.N), histochemically stained (Jefferson, 1987), and incubated for 24 hours at 37° C.; embryos were scored two days later. Excision of Ds from the test plasmid, due to the Ac-transposase activity in the bombarded tissue of transgenic plants, restored the functionality of the Act-gusA expression cassette thereby resulting in blue spots, which were counted undera microscope, on the bombarded tissue after histochemical staining.

The number of blue spots, which is an indicator of Ac transposase Li expression, showed a wide variability among plants from independent transformation events, as well as among plants derived from the same transformation event. Differences in the Ac-transposase expression level appeared to be the result of plant-to-plant variation rather than the promoter driving the Ac transposase gene. Ac activity was detectable in embryos at different developmental stages. The number of blue spots per embryo, however, was in general too low to observe significant differences in Ac-transposase expression at different stages of embryo development.

This example also illustrates that the transient Ac expression assay (McElroy et al., 1997) was reliable for characterizing transgenic plants. Ac activity could be detected in immature embryos of T1 and T2 plants as well as in later generations after crossing Ac-transposase and Ds-ubi-bar plants. Expression levels in these experiments were similar to those observed in earlier reports on barley callus (McElroy et al., 1997). The correlation between Ac-transposase activity in bombarded F2 embryos and in F2 plants themselves makes this assay a simple and valuable tool for screening plants for high transposition frequencies. This test is especially useful for targeted tagging strategies when transposed Ds elements have to be reactivated and visual excision markers, as they are commonly used in dicots, cannot be used.

Example 3

Transactivation of Ds by Ac Transposase in Stably Transformed Plants

Plants exhibiting Ac-transposase activity in bombarded embryos, as judged it the transient assay, were used for crosses with Ds-containing plants. After crossing Ac transposase-expressing plants with Ds-containing plants, the resulting F1 plants showed a low transposition frequency of Ds. Three F1 plants of a total of 144 tested plants showed a change in the Ds integration pattern after DNA hybridization analysis (data not shown). The observed excisions and reinsertions occured in somatic tissue exclusively. Selfing of F1 plants carrying both the stabilized Ac-transposase gene and the Ds element resulted in a striking increase in transposition frequencies in the subsequent F2 generation. Progeny of 24 different F1 plants that were derived from 10 independent crosses with different parents were analyzed. The F2 plants of 18 of these 24 parent plants showed evidence of transposition (Table 1). PCR analysis of empty donor sites resulted in the generation of a specific 300 bp PCR product, which is only amplified after excision of the complete 3.6 kbp Ds-Ubi-bar fragment from the original integration site. This confirmed that-the new banding patterns in the DNA hybridization blots were due to transpositions.

The transposition frequencies in F2 plants derived from independent F1 parents varied from 0% to 47%. Upon taking into account the differences in copy number of the Ds element in different F1 plants, the observed transposition frequencies ranged from 0% to 38% per introduced Ds element. Transposition frequencies of F2 plants I—, derived from F1 plants with the same parents were similar (see, for example, the F2 plants of A1-1, A1-5 and A1-8 in Table 1) indicating that differences in transposition frequencies in these plants were more likely due to the Ac-transposase expression level in the original parental Ac-transposase-containing plant than to plant-to-plant variation in transposase expression.

A significant correlation between somatic transposition frequency and the nature of the promoter driving the Ac transposase gene was not observed. F2 plants of line A18-5, for example, carrying Ac transposase under control of the relatively strong ubiquitin promoter, exhibited a very similar transposition frequency to F2 plants of line A18-5 where Ac transposase is driven by the relatively weak Ac promoter sequence. Similarly, the Ac copy number did not significantly influence the transposition frequency when either promoter was used, although copy number and level of expression are not correlated when direct DNA introduction methods are used. Analysis of the results of Ac activity assays performed on F2 immature embryos showed a direct correlation between Ac expression in F2 immature embryos and transpositions in F2 plants (Table 1).

TABLE 1

Frequency of transposition events in F2 plants from different F1 plants

| F1Plant | Promoter[1] used for Ac TPase | # F2 Plants analyzed[2] | average # blue spots per embryo[3] | # with Tnp[4] | % Tnp[5] |
|---|---|---|---|---|---|
| A1-1 | Ubi-1 | 40 | 1.1 | 7 | 23 |
| A1-5 | Ubi-1 | 100 | 0.9 | 16 | 20 |
| A1-8 | Ubi-1 | 40 | 0.5 | 5 | 16 |
| A8-1 | Ubi-1 | 200 | 1.4 | 57 | 38 |
| A8-5 | Ubi-1 | 100 | 1.2 | 25 | 33 |
| A12-1 | Ubi-1 | 20 | N.D. | 4 | 27 |
| A12-2 | Ubi-1 | 20 | N.D. | 3 | 20 |
| A15-1 | Ubi-1 | 20 | N.D. | 1 | 7 |
| A15-3 | Ubi-1 | 20 | N.D. | 0 | 0 |
| A20-7 | Ubi-1 | 20 | N.D. | 2 | 13 |
| A20-8 | Ubi-1 | 20 | 0 | 0 | 0 |
| A20-11 | Ubi-1 | 20 | 0.7 | 3 | 20 |
| A20-13 | Ubi-1 | 20 | ND. | 1 | 7 |
| A2-3 | Ac | 20 | 0 | 0 | 0 |
| A2-8 | Ac | 20 | 0 | 0 | 0 |
| A3-1 | Ac | 100 | 0.2 | 0 | 0 |
| A3-5 | Ac | 20 | N.D. | 3 | 20 |
| A5-7 | Ac | 20 | N.D. | 0 | 0 |
| A-8 | Ac | 20 | N.D. | 2 | 13 |
| A10-1 | Ac | 20 | 1.1 | 4 | 27 |
| A10-2 | Ac | 20 | 2.1 | 7 | 47 |
| A18-2 | Ac | 20 | 0.3 | 1 | 7 |
| A18-3 | Ac | 60 | 1.1 | 11 | 24 |
| A18-5 | Ac | 160 | 1.4 | 32 | 27 |

[1]Promoter used to regulate Ac transposase expression
[2]Number of F2 plants analyzed from specified F1 plant
[3]Average number of blue spots per bombarded embryo after Ac activity test
[4]Based on DNA hybridization analysis, number of F2 plants showing new bands (transpositions, tnp) relative to parent
[5]number of plants with transposition as a percent of plants carrying Ds elements Of the F$_2$ plants, 100% showed stable inheritance of the single copy, selectable marker gene, in striking contrast to the loss of expression in a significant fraction of comparable plants containing single copies of the selection gene, but that had not moved from the original location (Table 2) and to the frequency observed in T1 plants in earlier studies (65% of T1 generation plants had unstable expression characteristics. Wan and Lemaux, 1994).

TABLE 2

Summary of transgene expression stability test. Functional expression of bar (as measured by sensitivity to the herbicide Basta) in plants containing the transgene in its original integration site vs. expression of bar in plants containing the transgene in a new location after transposition of the Ds-Ubi-bar cassette

| Plant line | # of Basta resistant plants | # of Basta sensitive plants | # Basta sensitive plants containing the bar gene |
|---|---|---|---|
| Nontransposed bar[2] | | | |
| A8-1-5 | 40 | 16 | 2 |
| A8-1-232 | 39 | 0 | 0 |
| A8-5-2 | 39 | 3 | 3 |
| A8-5-17 | 32 | 13 | 2 |
| A8-5-20 | 28 | 16 | 8 |
| A8-5-21 | 16 | 8 | 3 |
| A18-5-3 | 40 | 1 | 1 |
| A18-5-6 | 36 | 3 | 3 |
| TOTAL | 270 | (60) | 22 |
| Transposed bar[1] | | | |
| A8-1-3 | 42 | 12 | 0 |
| A8-1-186 | 35 | 0 | 0 |
| A8-1-189 | 32 | 9 | 1 |
| A8-1-227 | 29 | 8 | 0 |
| A8-5-7 | 21 | 9 | 0 |
| A8-5-10 | 28 | 12 | 2 |
| A8-5-11 | 28 | 9 | 0 |
| A8-5-25 | 31 | 8 | 0 |
| A8-5-55 | 32 | 9 | 0 |
| A8-5-56 | 47 | 0 | 0 |
| A8-5-58 | 35 | 11 | 0 |
| A8-5-92 | 46 | 11 | 0 |
| A8-5-93 | 34 | 9 | 1 |
| A8-5-97 | 38 | 0 | 0 |
| A18-5-43 | 29 | 9 | 1 |
| A18-5-46 | 42 | 0 | 0 |
| A18-5-48 | 39 | 9 | 0 |
| A18-5-80 | 45 | 0 | 0 |
| A18-5-110 | 43 | 0 | 0 |
| TOTAL | 676 | (125) | 5 |

[1]Plants carrying a single copy of Ds-Ubi-bar in a new location.
[2]Control plants without transposition of Ds-Ubi-bar.

Fifteen different F2 plants derived from independent crosses that carried both Ac and Ds were selfed. The resulting F3 immature embryos continued to express Ac-transposase. F3 plants were analyzed by DNA blot hybridisation for transposition of Ds and showed transposition frequencies similar to those observed in F2 (Table 3).

TABLE 3

Transmittance of transposed Ds elements from F2 to F3 plants and new transpositions in F3 plants

| F2 plant | Promoter used for Ac TPase | % of F3 plants carrying the new insertion site observed in F2 parent | co-segregation of old and new insertion sites in F3 plants | % of Tnp in F3 |
|---|---|---|---|---|
| A1-5-10 | Ubi-1 | 100 | yes | 10 |
| A1-5-36 | Ubi-1 | 40 | no | 10 |
| A1-5-40 | Ubi-1 | 80 | yes | 15 |
| A1-5-671 | Ubi-1 | 30 | yes | 10 |
| A1-5-67[1] | Ubi-1 | 65 | no | 10 |
| A1-5-87 | Ubi-1 | 45 | yes | 15 |
| A1-5-89 | Ubi-1 | 80 | yes | 15 |
| A8-1-3 | Ubi-1 | 75 | yes | 40 |
| A8-1-7 | Ubi-1 | 75 | no | 15 |
| A8-1-27 | Ubi-1 | 35 | yes | 20 |
| A10-2-6 | Ac | 80 | yes | 25 |
| A10-2-13 | Ac | 75 | yes | 15 |
| A10-2-20 | Ac | 80 | yes | 20 |
| A18-5-9 | Ac | 75 | no | 20 |
| A18-5-13 | Ac | 75 | yes | 25 |
| A18-5-27 | Ac | 70 | yes | 15 |

[1]F2 plant A1-5-67 has two new Ds insertion sites as compared to the F1 parent

Example 4

Timing of Ds Transposition

Molecular analyses of F2 and F3 plants by DNA blot hybridization allowed us to draw conclusions regarding the timing of transpositions. Many F2 plants derived from A8-1, for example, exhibited the same Ds banding pattern. This indicates that a somatic transposition of Ds occurred early in development of the F1 plant, which affected a sector of the plant and was transmitted through the germline, thereby resulting in the same Ds integration pattern occurring in many F2 plants. Analysis of F3 plants, derived from selfed F2 plants with a new Ds integration site but without Ac-transposase, showed that the transposed Ds Element is stably transmitted to the next generation in its original location.

Most of the transpositions, however, resulted in a unique new banding pattern among the F2 plants. These unique integration sites could be due to either germinal transpositions in F1 or to somatic transpositions in F2 plants. Germinal transpositions in F1 resulted in F2 plants that are heterozygous for the new integration site of Ds. Selfing of these, Ac-transposase negative, plants resulted in a segregation ratio in the F3 generation close to 3:1 of plants carrying the transposed element versus plants without transposed Ds.

Somatic transpositions in the F2 generation may have occurred early or late in plant development. Late transpositions affected only small sectors in F2 plants and were likely not transmitted through the germline and were therefore either not detectable in the F3 generation, or resulted in an aberrant segregation ratio of the new Ds integration site in F3 plants. Early transpositions, on the other hand, were much more likely to be transmitted to the next generation and resulted in an expected 3:1 segregation of the new Ds site among the F3 plants.

Example 5

Transposition of Ds to Unlinked Sites

DNA hybridization analysis of F3 plants revealed that about 25% of all new Ds insertions observed in F2 were due to transpositions to unlinked sites (and, therefore, that about 75% of reinserted elements were linked to the original integration site). Independent segregation of a new and old Ds integration sites in progeny of a selfed F2 plant (A1-5-67) was observed, thereby demonstrating that transposition was to an unlinked site. Plants, containing two Ds loci after the transposition, segregated in a ratio which was similar to the expected 9:3:3:1 segregation ratio.

It is important for both tagging and gene delivery experiments in heterologous systems that the preference of Ds to transpose to an unlinked site is retained after introduction into the new host. A strong tendency of Ac and Ds to transpose to genetically linked sites has been observed in studies on maize (Greenblatt, 1984; Dooner, H. K. and Belachew, A., 1989) as well as in several heterologous systems (Jones et al., 1990; Dooner et al., 1991; Osborne et al., 1991; Healy et al., 1993; Bancroft, I. and Dean, C., 1993; Keller et al., 1993). Transposition frequencies to linked sites in these systems are high but may differ depending on the original integration locus. The frequency reported in barley is comparable to other systems and is frequent enough to allow for successful and efficient tagging experiments. It is noted that Ds elements in different transformants transposed to linked or unlinked sites in significantly different frequencies. Similar observations were made in tobacco (Dooner et al., 1991) and in tomato (Knapp et al., 1994) and are probably due to the chromatin structure in vicinity to the Ds donor site (Dooner et al., 1991).

Example 6

Reactivation of Transposed Ds Elements

In order to demonstrate the suitability of the transposon system in barley disclosed herein for targeted gene tagging by reactivation of transposed Ds elements in the vicinity of a gene of interest, we crossed plants containing a single transposed Ds element (A8-1-8 and A18-5-43) but containing no Ac transposase, with Ac-transposase-expressing plants in which Ac transposase is either transcriptionally controlled by the maize ubiquitin-1 promoter or the putative Ac-transposase promoter region. The resultant $F_1$ plants showed evidence of Ds transposition when the transposase gene was driven by the Ac promoter. Higher transposition frequencies were observed in progeny of selfed $F_1$ w plants regardless of the promoter used to drive the Ac transposase compared to the $F_1$ plants themselves. These data show that the reactivated Ds elements behave similarly to the Ds elements of primary transformants.

Conclusions from Examples 1–6

Intensive analysis of six generations of Ac-transposase and Ds-containing plants by DNA hybridization and PCR analyses proved the functionality of our transposon system. $F_2$ plants containing both elements and expressing the transposase gene showed evidence of Ds excisions and reinsertions. The observed frequencies of Ds transpositions varied over a large range but were comparable to those in many tagging systems in dicots (Jones et al., 1989; Jones et al., 1991; Hehl, R. and Baker, B., 1990; Rommens et al., 1992; Scofield et al., 1992). In a similar two element tagging system in rice (Izawa et al., 1997) the transposition frequency was not accurately determined but was sufficiently high to generate several phenotypic mutants that appeared to be linked to a Ds element.

In the single copy Ds line A8-1, 56% of all F2 plants containing the Ds element showed evidence of transposition. Transposition frequencies remained high in the next generation when Ac-transposase and Ds containing plants were selfed. Lines containing four (A18-5), five (A1-5) or more copies (A10-1) of Ds exhibited even higher transposition frequencies even though the frequencies per Ds element were lower than in line A8-1. Lines with these transposition frequencies are promising for tagging experiments. The results of experiments in which transposed Ds elements were reactivated indicate that high transposition frequencies are not restricted to the original integration site of the element and that transposed Ds elements can be used for further experiments with the same efficiency.

Higher levels of transposase expression are often associated with transpositions in developmentally earlier stages (Long, D. et al., 1993; Jones et al., 1989; Keller et al., 1993; Balcells, L. and Coupland, G., 1994) leading to large somatic sectors, which often transmit the transposed element through the germline and result in many siblings carrying the same transposition pattern. Plants carrying the Ac transposase under control of the ubiquitin promoter (lines A8-1 and A8-5 for example) often exhibited this characteristic In plants containing the Ac transposase gene driven by the Ac promoter (A18-3 and A 18-5), on the other hand, a large proportion of the transpositions occurred in very late developmental stages or in the germline, and their progeny showed a high number of independent transpositions. Similar results were obtained in experiments with *Arabidopsis* when the Ac promoter was used for Ac-transposase expression (Bancroft, I. and Dean, C., 1993). In the experiments described in the Examples, comparison of transposition events shows that transcriptional control of the transposase gene by the Ac promoter region led, in most cases, to higher germinal transposition frequencies than when transcription was controlled by the maize ubiquitin promoter (Table 3).

Example 7

Functional Expression of Ac-Transposase in Wheat

The Ac-transposase/Ds maize TE system is also functional in wheat. The functionality of the expressed Ac-transposase were monitored using a transient assay for Ac-transposase activity (McElroy, et al., 1997). T1/T2 immature embryos (1.5 to 3.0 mm in length) of plants confirmed molecularly as containing either AcAc-transposase or UbiAc-transposase were bombarded with a test construct carrying an ActI-gusA expression cassette interrupted by a Ds insert (FIG. 1, plasmid pSPWDV-Act1 (Dsbar)-GUS.N), histochemically stained (Jefferson, 1987), and incubated for 24 hours at 37° C.; embryos were scored two days later. Excision of Ds from the test plasmid, due to the Ac-transposase activity in the bombarded tissue of transgenic plants, restored the functionality of the Act-gusA expression cassette thereby resulting in blue spots, which were counted under a microscope on the bombarded tissue after histochemical staining. The results of the analysis are shown in Table 4.

TABLE 4

Functional expression of Ac transposase in immature embryos of wheat and Ac-transposase-mediated excission of Ds from test plasmid pSP-WDV-Act1(Ds-Ubi-bar)-Gus after transient co-transformation with pSP-WDV-ACT1(Ds-Ubi-bar)-Gus and pSP-Ubi-Ac results in expression of the reporter gene.

| Plasmid used for bombardment | Average # of blue spots per embryo |
|---|---|
| control without bombardment | 0 |
| pSP-WDV-Act1(Ds-Ubi-bar)-Gus | 0 |
| pSP-Ubi-Ac | 0 |
| pSP-WDV-Act1(Ds-Ubi-bar)-Gus + pSP-Ubi-Ac | 61 |

The examples thus illustrate that the transposon system of the invention has the full functionality of a two element transposon system and is functional in barley and wheat.

Having described the principles of the invention and provided illustrative embodiments, it will be apparent to one of skill in the art that the invention can be modified without departing from the scope and spirit of the claims set forth below. All references cited herein are incorporated into the application.

REFERENCES

1. Aarts, M. G. M. et al., *Nature,* 363:715–717 (1993)
2. Ainley et al., *Plant Mol. Biol.* 22:13–23 (1993)
3. An et al., *Plant Physiol.* 88:547 (1988)
4. Assaad et al., *Plant Mol. Bio.* 22: 1067–1085 (1993)
5. Ausubel et al., *Current Protocols in Molecular Biology* (1987)
6. Baker et al., *Proc. Natl. Acad Sci USA* 83: 4844–4848. (1986)
7. Balcells, L. and Coupland, G., *Plant Mol. Biol.* 24, 789–798 (1994)
8. Bancroft, I. and Dean, C., *Genetics* 134, 1221–1229 (1993)
9. Bancroft, I. et. al., *Plant Cell,* 5:631–638. (1993).
10. Baulcombe *Plant Mol. Bio.* 32:79–88 (1996)
11. Benfey et al., *Scienc.,* 250:959–966. (1990)
12. Bustos et al., *Plant Cell,* 1:839. (1989)
13. Bourque *Plant Sci.* (Limerick) 105:125–149 (1995)
14. Callis et al., *Plant Physiol.,* 88:965. (1988)
15. Carpenter et al, *The Plant Cell,* 4:557–571. (1992)
16. Chan and Glazer *J. Mol. Medicine* (Berlin) 75:267–282 (1997)
17. Cho, MJ et al., *Plant Science,* in press (1998)
18. Cho et al., *Theoretical Appl. Genet.* 98:1253–1262 (1999)
19. Christensen, A. and Quail P., *Transgenic Research,* 5:213–218. (1996).
20. Chuck, G. et al., *Plant Cell,* 5:37 1–378 (1993)
21. Cone, K., *Maize Gen. Coop. Newsletter* 63, 68 (1989)
22. Coupland, G. et al., *EMBO J.,* 7:3653–3659 (1988)
23. Dekeyser et al, *Plant Cell,* 2:59 1 1988 (1990)
24. Denis et al., *"Plant Physiol.,* 101:1295–1304 (1993)
25. Dooner, H. K. and Belachew, A., *Genetics* 122, 447458 (1989)
26. Dooner et at, *Plant Cell* 3, 473482 (1991)
27. Earp, D. et al., *Nucl. Acids Res.,* 18:3271–3279 (1990).
28. Eastham and Ahlering *J. Urology* 156:1186–1188 (
29. Ellis, J. G. et al., *Theor. Appl. Genet.,* 85:46–54 (1992)
30. Federoff *American Society for Microbiology,* Washington, DC pp 375411. (1989)
31. Flavell Proc. *Natl. Acad. Sci. USA* 91: 3490–3496 (1994)
32. Fromm et al., *Plant Cell,* 1:977 (1989)
33. Fromm, M E; et al., *Bio-Technology,* 8:833–839 (1990)
34. Gatz et al., *Ann. Rev. Plant Physiol. Plant Mol. Biol.,* 48:89–108. (1997)
35. Gelvin et al., *Plant Molecular Biology Manual,* (1990)
36. Gerats, A. G. M. et al, *Dev. Genet.,* 10:561–568. (1989)
37. Gierl and Saedler *Plant Mol. Biol.,* 19: 39–49 (1990)
38. Gilmartin et al., *The Plant Cell,* 4:839–949 (1992)
39. Giovannangeli et al., *Biochemistry* 35:10539–10548 (1996)
40. Haring, M. A. et al., *Plant Mol. Biol.,* 13:189–201 1989
41. Haseloff et al., *Nature,* 334:585–591 (1988)
42. Havre and Glazer *J. Virology* 67:7324–7331 (1993)
43. Healy et al., *Genetics* 134, 571–584 (1993)
44. Hehl, R. and Baker, B., *Plant Cell* 2, 709–722 (1990)
45. Heiser et al., *Plant Sci.* (Shannon) 127:61–69 (1997)
46. Hiatt et al., U.S. Pat. No. 4,801,340
47. Innis et al., (eds.) PCR Protocols, *A Guide to Methods and Applications* (1990)
48. Izawa et al., *Plant Mol. Biol.,* 35:219–229-(1997)
49. Jahne et al., *Theor. Appl. Genet.* 89:525–533 (1994)
50. Jefferson, R A et al., *EMBO Journal,* 6: 3901–3908 (1987)
51. Jensen et al., *Hereditas* (Lund) 129:215–225 91998)
52. Jones et al., *Science* 244, 204–207 (1989)
53. Jones et al., *Plant Cell* 2, 701–708 (1990)
54. Jones et al., *Maydica* 36, 329–335 (1991)
55. Jones, J. D. G. et al., 4th *Internatl. Congr. Plant Mol. Biol,* Amsterdam, June 19–24 (ISPMB), abs.: 1624 (1994)
56. Keller et al., *Theor Appl Genet* 86, 585–588 (1993)
57. Keller et al., *Plant Mol Biol* 21, 157–170 (1993)
58. Kihara et al., 26th *European Brewing Convention Congress,* Masstricht, Netherlands, *J. of the Institute of Brewing* 103:153 (1997)
59. Knapp, S. et al., *Mol. Gen. Genet.,* 213:285–290 (1988)
60. Kuhlemeier et al., *Plant Cell,* 1:471 (1989)
61. Lassner et al., *Mol. Gen. Genet.,* 218: 25–32 (1989)
62. Lalonde, et al., *Plant Molecular Biology* 34:445–453 (1997)
63. Lawrence, G. J., et al., *Cloning a rust resistance gene in flax. Seventh mt. Symp. On Molecular Plant-Microbe Interactions,* Univ. Edin., Scotland, June 26-July 1, abs.: 287 (1994).
64. Lawrence, G., et al., *Plant J,* 4:659–669 (1993)
65. Lemnaux, P G et al., *Bio-Rad US/KG Bulletin* 2007:1–6 (1996)
66. Long, D. et al., *Proc Nail. Acad. Sci, USA* 90, 10370–10374 (1993)
67. Marcotte et al., *Plant Cell,* 1:969 (1989)
68. McElroy et al., *Plant Cell* 2, 163–172 (1990)
69. McElroy et al., *Molecular and General Genetics* 231:150–160 (1991)
70. McElroy et al., *Molecular Breeding* 1, 27–37 (1995)

71. McElroy, D. et al., *Plant Journal* 11: 157–165 (1997)
72. Metzlaff et al., *Cell* 88: 845–854 (1997)
73. Miura et al., *Theoretical and Applied Genetics* 89:276–280 (1994)
74. Napoli et al., *The Plant Cell* 2:279–289 (1990)-
75. Odel et al., *Nature*, 313:8 10 (1985)
76. Opperman et al., *Science*, 263:221–223 (1993)
77. Osborne et al., *Genetics* 129, 833–844 (1991)
78. Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238
79. Prins and Goldbach *Arch. Virol.* 141: 2259–2276 (1996)
80. Rahman et al., *Theoretical and Applied Genetics* 90:156–163 (1999)
81. Rommens et al., *Mol. Gen Genet*, 231, 433–441 (1992)
82. Roshal et al., *EMBO J.*, 6:1155 (1987)
83. Sambrook et al., *In Molecular Cloning: A Laboratory Manual, Cold Spring Harbor*, N.Y. (1989)
84. Schaffner & Sheen *Plant Cell*, 3:997 (1991)
85. Schernthaner et al., *EMBO J*, 7:1249 (1988)
86. Scofield et al., *Plant Cell* 4, 573–582 (1992)
87. Sheehy et al., *Proc. Nat. Acad. Sci. USA*, 85:8805–8809 (1988)
88. Shimamoto et al., *Mol. Gen. Genet*, 239: 354–360 (1993)
89. Siebertz et al., *Plant Cell* 1:961 (1989)
90. Sokol and Murray *Transgenic Res.* 5:363–371 (1996)
91. Stam et al., *Annals Bot.* 79: 3–12 (1997)
92. Stockhause et al., *The Plant Cell* 9:479–489 (1997)
93. Stougaard *The Plant Journal* 3(5): 755–761 (1993).
94. Sun et al., *Mol. Biotechnology* 7:241–251 (1997)
95. Terada & Shimamoto *Mol. Gen. Genet.* 220:3 89 (1990)
96. Sluys, M. A. et al., *EMBO J*, 6:3881–3889 (1987)
97. Voeroes et al., *Eur. J. of Biochem.* 251:36–44 (1998)
98. Walbot, V. Ann. Rev. *Plant Physiol. Plant Mol. Biol.*, 43:4982 (1992)
99. Wan, Y. et al., *Plant Physiology* 104:3 7–48 (1994)
100. Weissbach & Weissbach *Methods for Plant Molecular Biology, Academic Press* (1989).
101. Whitham, S. et. al., *Cell* 78:1101–1115 (1994)
102. Wirtz et al., *Plant Journal* 11, 125-135(1997)
103. Yang, C. H. et al., *Plant Mol. Biol.*, 22:793–805 (1993)
104. Yoder, J. L. et al., *Mol. Gen. Genet.*, 213:291–296 (1988)
105. Zhou, J. H. et al., *Plant Cell Rep.* 8:542–545 (1990)
106. Zhao and Pick *Nature* 365:448451 (1993)

What is claimed is:

1. A method of generating a stably transformed barley plant comprising a stably expressed transgene, the method comprising introducing a Ds element comprising the transgene into a barley plant and introducing a nucleic acid sequence encoding an Ac transposase into the barley plant before or after the step of introducing the Ds element, whereby the Ds element comprising the transgene integrates into a barley plant genome through transposase-mediated excision; and selecting a barley plant in which the Ds element comprising the transgene is integrated, thereby obtaining the stably transformed barley plant comprising the stably expressed transgene.

2. The method of claim 1, wherein the introducing of the Ds element comprising the transgene is by bombardment-mediated transformation of barley plant cells followed by regeneration of barley plants from the cells.

3. The method of claim 1, wherein the introducing of the nucleic acid sequence encoding an Ac transposase is by a sexual cross.

4. The method of claim 1, wherein the nucleic acid sequence encoding an Ac transposase is in an Ac element.

5. The method of claim 4, wherein the Ac element is linked to a negative selectable marker.

6. The method of claim 5, wherein the negative selectable marker is codA.

7. The method of claim 1, wherein the step of selecting comprises selecting barley plants in which a single copy of the Ds element is integrated.

* * * * *